United States Patent [19]

Cutter

[11] 4,380,820
[45] Apr. 19, 1983

[54] COMPACT X-RAY COLLIMATOR

[75] Inventor: James W. Cutter, Hollister, Calif.

[73] Assignee: The Machlett Laboratories, Incorporated, Stamford, Conn.

[21] Appl. No.: 161,108

[22] Filed: Jun. 19, 1980

[51] Int. Cl.³ .............................................. A61B 6/06
[52] U.S. Cl. ................................................ 378/153
[58] Field of Search ................ 250/511, 513; 378/152, 378/153

[56] References Cited

U.S. PATENT DOCUMENTS

| 2,332,339 | 10/1943 | Pratt | 49/324 |
|---|---|---|---|
| 2,542,196 | 2/1951 | Haupt | 250/511 |
| 3,452,964 | 7/1969 | Bibeault | 49/324 |
| 3,829,701 | 8/1974 | Hura | |
| 3,936,647 | 2/1976 | Fekete | 250/511 |
| 3,947,690 | 3/1976 | Peyser | |
| 4,128,767 | 12/1978 | Stödberg | 250/513 |
| 4,246,488 | 1/1981 | Hura | 250/511 |

FOREIGN PATENT DOCUMENTS 1083402 9/1967 United Kingdom .

OTHER PUBLICATIONS

James et al., *Mathematics Dictionary*, Digest Press, Van Nuys Calif., 1946, pp. 62-63.

*Primary Examiner*—Alfred E. Smith
*Assistant Examiner*—T. N. Grigsby
*Attorney, Agent, or Firm*—John T. Meaney; Joseph D. Pannone; Richard M. Sharkansky

[57] ABSTRACT

An X-ray collimator comprising an X-ray shielded enclosure having aligned entrance and exit apertures for permitting passage of an X-ray beam, the exit aperture having a generally rectangular configuration defined by edges of two orthogonally disposed pairs of opposing rotatable exit shutter elements. Each of the exit shutter elements has a generally semi-cylindrical configuration and is concentrically disposed about a respective axis of rotation. Each pair of semi-cylindrical exit shutter elements is mounted for opposing rotatable movement within the other pair of semi-cylindrical exit shutter elements. The entrace aperture of the housing may be defined by two orthogonally disposed pairs of opposing shutter plates, one pair thereof being directly linked to an associated pair of semi-cylindrical exit shutter elements for corresponding movement therewith.

17 Claims, 14 Drawing Figures

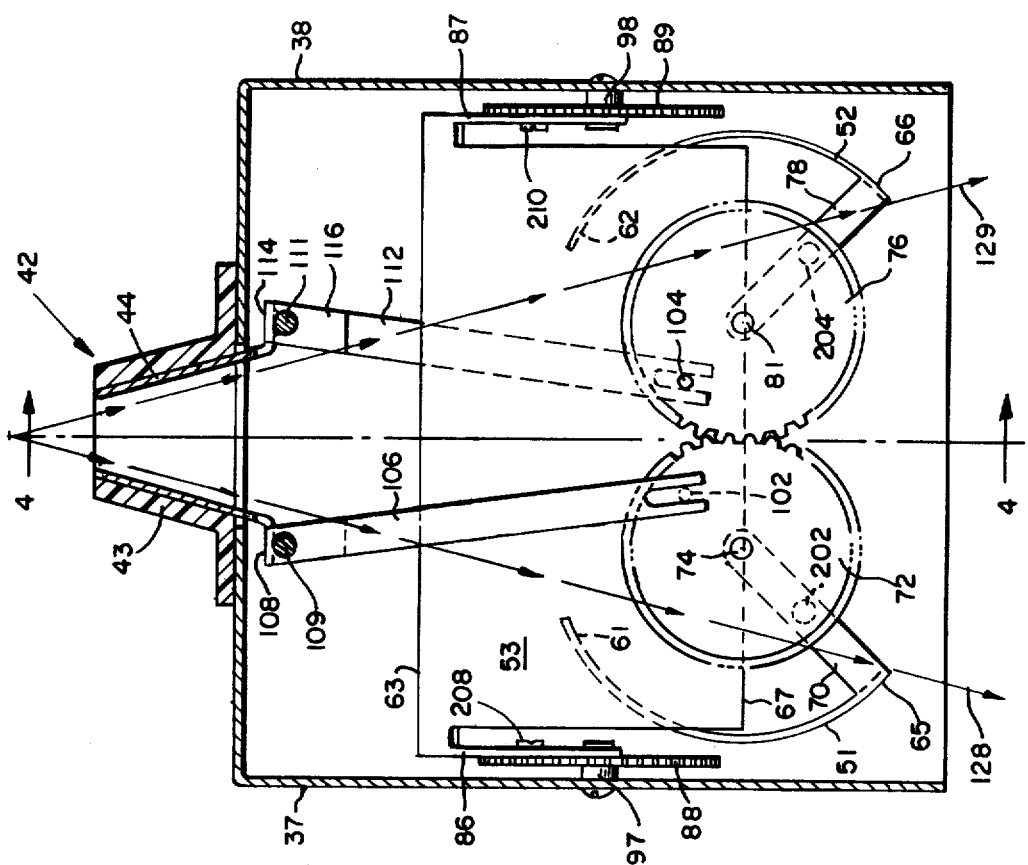
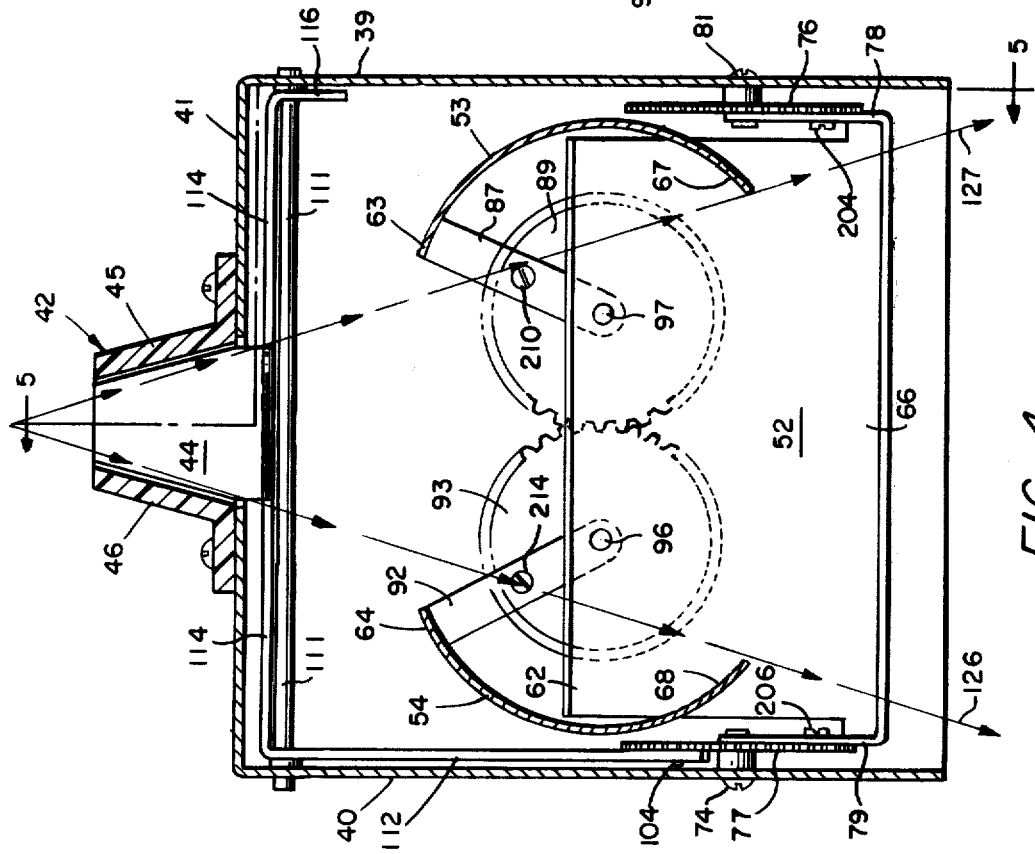
FIG. 5
FIG. 4

COMPACT X-RAY COLLIMATOR

BACKGROUND OF THE INVENTION

1. Field of the Invention

This invention relates generally to radiation collimator devices and is concerned more particularly with an X-ray collimator devices having a simplified and compact arrangement of shutter elements.

2. Discussion of the Prior Art

An X-ray generator usually comprises an oil-filled housing having therein an X-ray tube provided with an electron-emitting cathode and a spaced anode target. The cathode generally is disposed to direct a beam of electrons onto a small area, known as the "focal spot" area, of the anode with sufficient energy to generate X-rays in the target material. As a result, X-rays radiate from the focal spot area in all directions within the tube envelope. The useful portion of these X-rays pass, in the form of a conical beam, through an X-ray transparent window of a radially aligned port which is recessed in the wall of the housing. Thus, the focal spot area of the anode target ideally functions as a point source of the conical X-ray beam emanating from the port of the X-ray generator.

The X-ray beam may be directed, for example, through a selected region of a human patient for a limited interval of time, and impinge on an aligned surface area of a rectangular film. However, in order to protect the patient from over-exposure to X-radiation, it is required that the irradiated region of the patient be no larger than the effective area of the rectangular film. Accordingly, there may be mounted over the port of the X-ray generator a collimator device having therein suitable X-ray absorbent shutter elements for providing an adjustable exit aperture of the desired size. In this manner, the conical X-ray beam emanating from the port of the X-ray generator may be restricted by the collimator shutter elements to the proper cross-sectional size and configuration for conforming to the effective area of the rectangular film.

Some X-ray collimator devices of the prior art have a rectangular exit aperture defined by two orthogonally disposed pairs of opposing pivotal shutter plates. However, one pair of shutter plates is mounted for opposing pivotal movement in a plane above the other pair of shutter plates. Also, each of the orthogonally disposed pairs of shutter plates may require relatively complex drive means for adjusting the respective elements of each pair to provide desired aperture sizes. Consequently, the device having the shutter plates and required drive gearing, including entrance shutter-to-exit shutter linkages, may not lend itself to compactness or economy for situations where a compact and relatively inexpensive collimator is desired.

SUMMARY OF THE INVENTION

Accordingly, this invention provides a compact and simplified collimator suitable for relatively inexpensive fabrication having shutter means for providing an X-ray beam conforming to an area of an X-ray film cassette. The shutter means comprises two orthogonally disposed pairs of opposing rotatable exit shutter elements, each exit shutter element having an edge disposed for forming a portion of the periphery of an exit aperture of the collimator. Each exit shutter element has a generally semicylindrical configuration which is substantially concentric with its respective axis of rotation. Each pair of the semicylindrical shutters elements is adapted to rotate within the region bounded by the other pair to provide a compact structure. Further, the two pair of shutter elements are identical in construction and may be formed by a relatively inexpensive stamping process thereby reducing the cost of the collimator.

The collimator preferably includes an entrance shutter comprising two orthogonally disposed pairs of entrance shutter elements, one pair thereof being pivotally movable to define a portion of the entrance aperture. Each of the movable entrance shutter elements is directly linked to an associated exit shutter element for corresponding movement therewith.

BRIEF DESCRIPTION OF THE DRAWINGS

For a more complete understanding of this invention reference is made in the following detailed description to the drawings wherein:

FIG. 4 is a front sectional view showing the relationship of each of the exit shutter elements in a fully open position, such cross section being taken along line 4—4 in FIG. 5.

FIG. 5 is a side sectional view taken along the line 5—5 shown in FIG. 4 and looking in the direction of the arrows with the movable pair of entrance shutter elements and the pair of exit shutter elements coupled thereto in a fully open position.

DESCRIPTION OF THE PREFERRED EMBODIMENT

Figure 1:
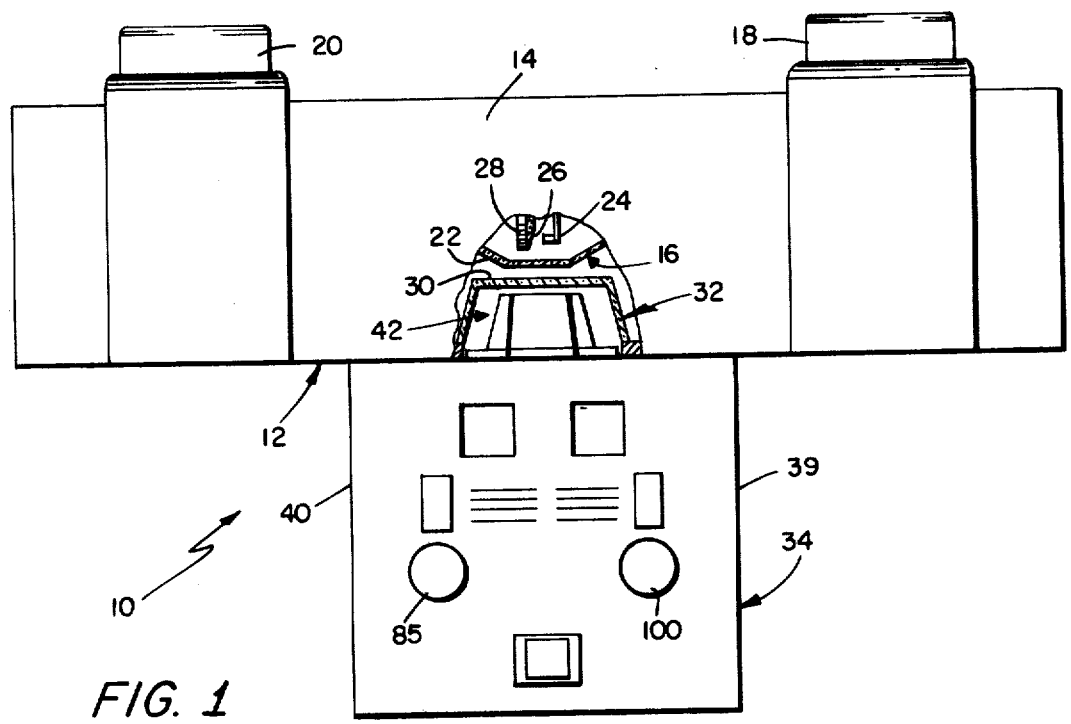
FIG. 1 is a pictorial view, partly in section, showing a collimator embodying this invention attached in operative relationship to the housing of an X-ray generator.

Referring to the drawings wherein like characters of reference designate like parts, there is shown in FIG. 1 an X-ray apparatus 10 which includes an X-ray generator 12 having a hollow cylindrical casing 14 wherein an X-ray tube 16 is longitudinally disposed. Casing 14 generally is filled with a dielectric coolant, such as oil, for example, and is provided with externally extending cable terminals 18 and 20, respectively, which provide means for applying respective electrical potentials to the electrodes of X-ray tube 16.

Within the envelope 22 of X-ray tube 16, an electron emitting cathode 24 is disposed to direct a beam of electrons onto a small focal spot area 26 of an anode target 28, which may be of the rotating type, for example. Electrons in the beam impinge on the focal spot area 26 with sufficient energy to generate X-rays which radiate therefrom in all directions. Consequently, the casing 14 generally is lined with suitable material, such as lead, for example, for absorbing a major portion of the unused X-rays emanating from the focal spot area 26.

The useful portion of the X-rays, thus produced, radiate from the focal spot area 26 in a conical-shaped beam which passes through an X-ray transparent window 30 of a radially aligned port 32. The port 32 is cup-shaped and recessed in the cylindrical wall of casing 14 such that the window 30 is disposed in close proximity to the focal spot area 26 of anode target 28. Thus, the focal spot area 26 functions as a point source of the conical X-ray beam passing through the adjacent window 30 of port 32. However, off-focus X-radiation generated in portions of the anode target 28 outside of the focal spot area 26 also may pass through the window 30 of port 32, usually at an angle with the axial centerline of the conical X-ray beam emanating from focal spot area 26. Mounted over the port 32 of generator 12, in a well-known manner, is an X-ray collimator 34 embodying this invention.

Figure 2:
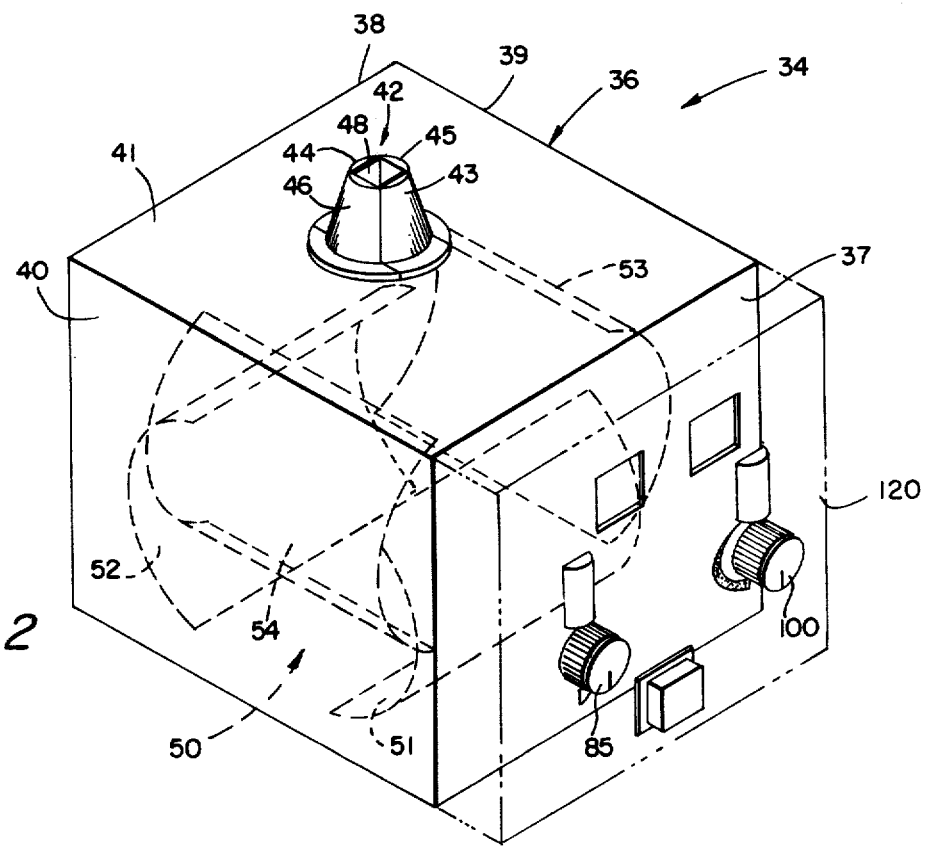
FIG. 2 is an isometric view of the collimator shown in FIG. 1.
Figure 3:
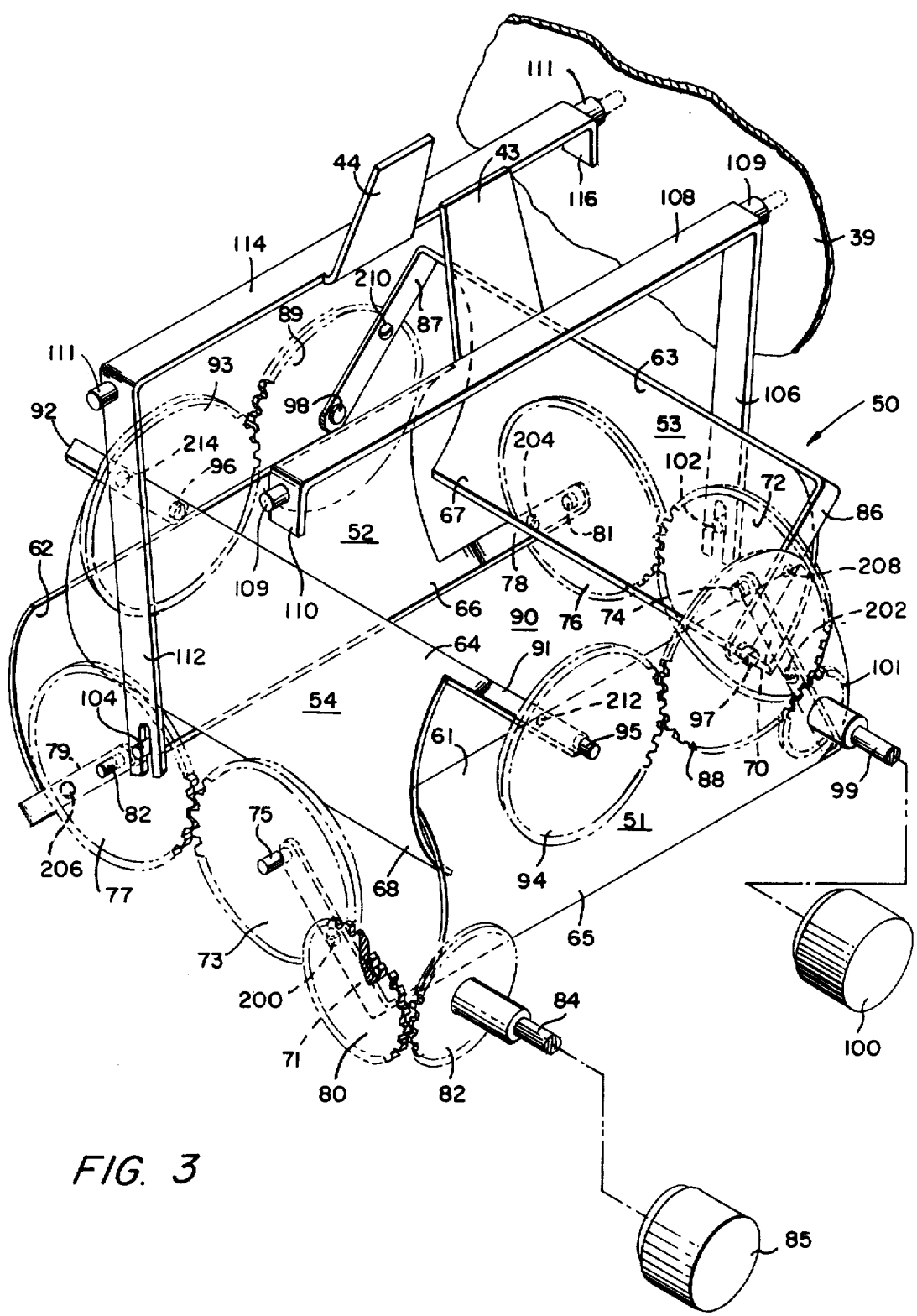
FIG. 3 is a schematic view showing the structural relaship of a pair of the movable entrance shutter elements and the two pairs of exit shutter elements shown in FIG. 2.

As shown in FIG. 2, the collimaor 34 includes an X-ray shielded enclosure or housing 36 provided with spaced opposing front and rear walls, 37 and 38, respectively, which are orthogonally disposed to spaced opposing side walls, 39 and 40, respectively. The walls 37-40 are orthogonally disposed to an entrance wall 41 from which may protrude an entrance shutter 42. Entrance shutter 42 extends into the cup-shaped recess of port 32 (FIG. 1) to dispose an adjustable entrance aperture 48 formed by the entrance shutter 42 in closed proximity with the focal spot area 26 of target 28. The entrance aperture 48 is disposed substantially in alignment with the focal spot area 26, and is adjusted to a size for permitting passage of the X-ray beam emanating therefrom while restricting passage of off-focus X-radiation. Entrance aperture 48 may have a rectangular configuration formed by four orthogonally disposed entrance shutter plates or elements, 43-46, respectively, made of X-ray absorbent material, such as lead, for example. Alternatively, the respective entrance shutter elements 43-46 may be made of lightweight material, such as aluminum, for example, which is coated with X-ray absorbent material, such as lead, for example. Also, the respective walls 37-41 of housing 36 may be made of suitably rigid material, such as sheet steel, for example, having surfaces provided with a layer of X-ray absorbent material, such as lead, for example. Thus, an economical lightweight housing may be fabricated by stamping and forming the walls 37-41 and lining the surfaces of the resulting structural parts with X-ray absorbing material.

Here the portion of housing 36 opposite the entrance wall 41 is open for permitting unrestricted passage of an x-ray beam collimated by shutter elements disposed within the housing 36, in a manner to be described, to emerge from the collimator 34 wth a cross-sectional area conforming to a suitable X-ray receptor (not shown). More particularly, the emerging collimated X-ray beam is provided with a desired cross-sectional size and shape in housing 36 by means of an exit shutter 50 disposed in alignment with the entrance aperture 48 formed by entrance shutter 42. Exit shutter 50 is comprised of a first pair of opposing exit shutter elements 51 and 52, respectively, which are orthogonally disposed with respect to a second pair of opposing exit shutter elements 53 and 54 respectively. The exit shutter elements 51-54 are orthogonally disposed with respect to the centerline of the exit shutter 50 (i.e. the axis of the collimator disposed normal to the entrance wall 41 and passing through the center of the entrance and exit apertures).

The exit shutter elements 51-54 are curved, with respect to such centerline, concavely when viewed from a region within the exit shutter 50. Each of the exit shutter elements 51-54 is disposed in registration with a respective one of the entrance shutter elements 43-46. Preferably each of the exit shutter elements 51-54 has a substantially semi-cylindrical surface disposed about a respective longitudinal axis orthogonal to the centerline of the collimator. Each one of the exit shutter elements 51-54 is adapted to rotate about its respective longitudinal axis in a manner to be described hereafter. Suffice it to say here however, that the lower longitudinal edge of each one of the exit shutter elements 51-54 defines a respective peripheral portion of the generally rectangular shaped exit aperture. The length of the exit aperture is related to the separation between the lower longitudinal edges of one pair of opposing exit shutter elements 51-54; and the width of the exit aperture is related to the separation between the lower longitudinal edges of the other pair of opposing exit shutter elements.

As shown in FIGS. 3-8, a pair of opposing exit shutter elements 51 and 52 have respective upper longitudinal edge portions 61 and 62 disposed to rotate arcuately into a region between a pair of orthogonally disposed exit shutter elements 53-54 and below respective upper longitudinal edge portions 63 and 64 thereof. The exit shutter elements 51 and 52 have opposing lower longitudinal edge portions, 65 and 66, respectively, which define one dimension of a rectangular exit aperture 90; and the exit shutter elements 53 and 54 have opposing longitudinal lower edge portions, 67 and 68, respectively, which define the other dimension of rectangular exit aperture 90. The lower edge portion 65 of exit shutter element 51 extends longitudinally beyond respective arcuate ends of the element 51 and is bent orthogonally to form radially extended legs 70 and 71, respectively. Each of the legs 70 and 71 extends radially of a respective spur gear 72 and 73 and is fixedly attached thereto by screws 200, 202 so that the legs 70 and 71 and the spur gears 72, 73 rotate as a single unit, about the longitudinal centerline of semi-cylindrical shutter element 51. The spur gears 72 and 73 have central apertures through which respective axle pins 74 and 75 extend and are bearingly mounted in side walls 39 and 40, respectively, of housing 36.

The spur gears 72 and 73 intermesh with respective spur gears 76 and 77 having fixedly attached to their inner surfaces, as by screws 204 and 206, for example, radially extending legs, 78 and 79, respectively. The legs 78 and 79 constitute orthogonally bent end portions of the longitudinal lower edge portion 66 which extends beyond arcuate ends of the exit shutter element 52. The spur gear 76 has a central aperture aligned with a central aperture in spur gear 77 through which respective axle pins 81 and 82 extend and are bearingly mounted in respective side walls 39 and 40 of housing 36. The spur gear 73 meshes with a combination spur-beveled idler gear assembly 80 which, in turn meshes with a beveled drive gear 82 having extended centrally through it a rotatable shaft 84 bearingly mounted in front wall 37. An externally extended end portion of shaft 84 may have affixed thereto a suitable knob 85 which provide means for manually rotating shaft 84 and the intermeshed gears 72–73 and 76–77 to rotate the respective exit shutter elements 51 and 52 in opposing angular directions about their respective axial, or longitudinal centerlines.

As a result, upper longitudinal edge portions 61 and 62 of exit shutter elements 51 and 52, respectively, move arcuately toward or away from one another within the region defined by the orthogonally disposed exit shutter elements 53 and 54, respectively. Also, the opposing lower longitudinal edge portions 65 and 66 are positioned relative to one another for defining an interposed dimension of the rectangular exit aperture 90. The other dimension of rectangular exit aperture 90 is defined by relative positioning of the lower longitudinal edge portions 67 and 68 of exit shutter elements 53 and 54 which move arcuately toward and away from one another in a region defined by orthogonally disposed exit shutter elements 51 and 52, respectively. The exit shutter elements 53 and 54 curve envelopingly around respective adjacent arcuate ends of the shutter elements 51 and 52, and have respective upper longitudinal edge portions 63 and 64 positioned relative to one another in a region overlying the upper longitudinal edge portions 61 and 62 of shutter elements 51 and 52, respectively.

Upper edge portion 63 extends longitudinally beyond the opposing arcuate ends of exit shutter element 53, and is bent orthogonally to form respective radially extending legs 86 and 87. The legs 86 and 87 extend radially of respective spur gears 88 and 89 to which they are fixedly attached by screw 208, 210 so that legs 86, 87 and spur gears 88, 89 rotate as a single unit about the aligned axial centerlines of gears 88 and 89. Similarly, upper longitudinal edge portion 64 of shutter element 54 extends longitudinally beyond the opposing arcuate ends of the exit shutter element 54, and is bent orthogonally to form respective radially extending legs 91 and 92. The legs 91 and 92 extend radially of respective spur gears 93 and 94 to which they are fixedly attached by screws 212, 214 so that the exit shutter element 52 and the fixedly attached spur gears 93, 94 rotate as a single unit about the aligned axial centerlines of gears 93 and 94. The gears 93 and 94 have aligned central apertures through which respective axle pins 95 and 96 extend and are bearingly mounted in front and rear walls 37 and 38, respectively, of housing 36. Also, the gears 88 and 89 have aligned central apertures through which respective axle pins 97 and 98 extend and are bearingly mounted in the front and rear walls 37 and 38, respectively, of housing 36.

The spur gear 88, for example, may be rotatably coupled through a spur gear 101 to a shaft 99, rotatably mounted in front wall 37 of housing 36. The shaft 99 may be provided with an externally protruding end portion to which may be fixedly attached a suitable knob 100 for manually rotating shaft 99, gear 101, and intermeshed gears 88–89 and 93–94. Thus, the exit shutter elements 53 and 54 may be rotated in respective opposing angular directions about their axial or longitudinal centerlines to travel arcuately around adjacent end portions of exit shutter elements 51 and 52, respectively, and move into or out of the region defined by orthogonally disposed shutter elements 51 and 52, respectively. As a result, in the region defined by orthogonally disposed exit shutter elements 51 and 52, the respective longitudinal edge portions 67 and 68 of the opposing shutter elements 53 and 54 move arcuately toward or away from one another to define the interposed dimension of exit aperture 90.

Figure 9A:
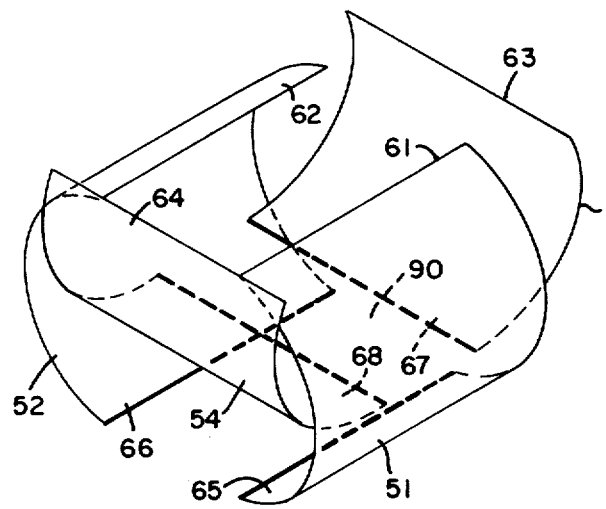
FIGS. 9A-9D are respective diagrammatic views showing the operational relationship of the exit shutter elements comprising the exit shutter shown in FIG. 3 in various positions.
Figure 9B:
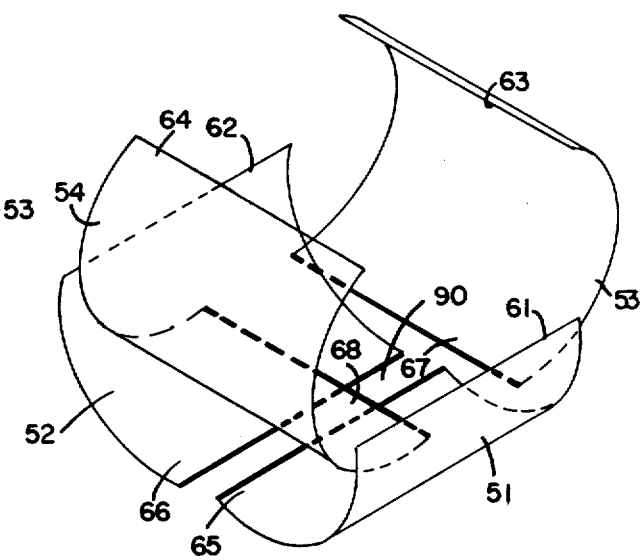
Figure 9C:
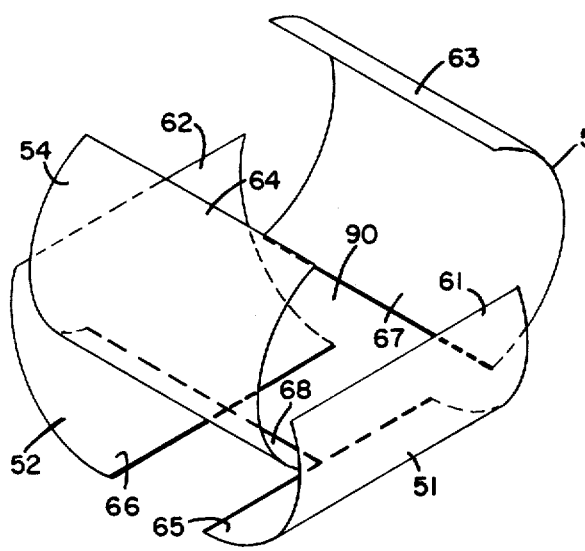
Figure 9D:
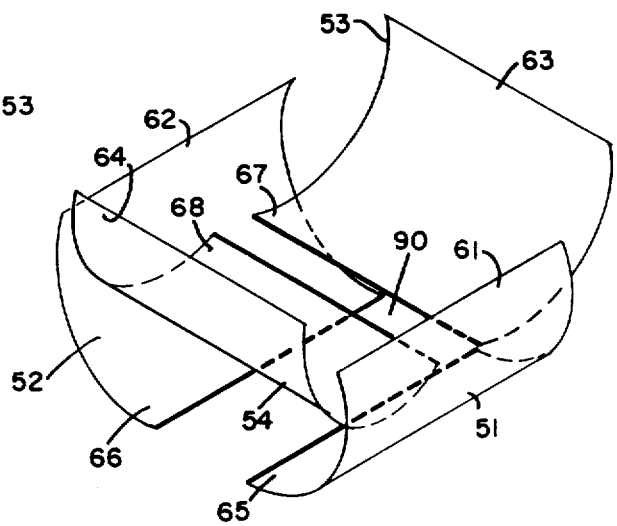

Accordingly, the respective exit shutter elements 51 and 52 may be adjusted independently of the respective exit shutter elements 53 and 54 to define an interposed dimension of the exit aperture 90 which may be relatively large, as shown in FIG. 9A, or which may be relatively small, as shown in FIG. 9B. Also, the respective exit shutter elements 53 and 54 may be adjusted independently of the respective exit shutter elements 58 and 59 to define an orthogonal dimension of exit aperture 90 which may be relatively large, as shown in FIG. 9C, or which may be relatively small, as shown in FIG. 9D. This independence of adjustment is achieved by disposing the respective pairs of semi-cylindrical exit shutter elements 51–52, and 53–54 in enfolding relationship with one another. The semi-cylindrical exit shutter elements 51–54 are supported at their respective opposing end portions and rotated about their respective longitudinal axes such that longitudinal edge portions of one pair is enabled to move arcuately within a region defined by the orthogonally disposed elements of the other pair. As a result, longitudinal edge portions of the respective pairs of exit shutter elements are enabled to share a common region between the longitudinal edge portions of the other pair to produce the very compact collimator 34.

Figure 10:
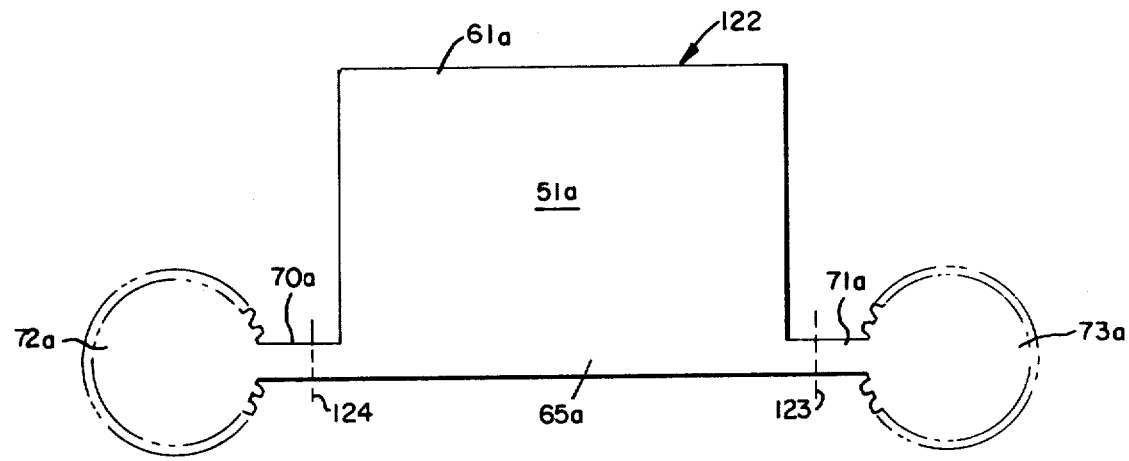
FIG. 10 is a plan view of exit shutter element suitable for use in the collimator shown in FIG. 1 at a stamping stage in the manufacture thereof and prior to forming.
Figure 11:
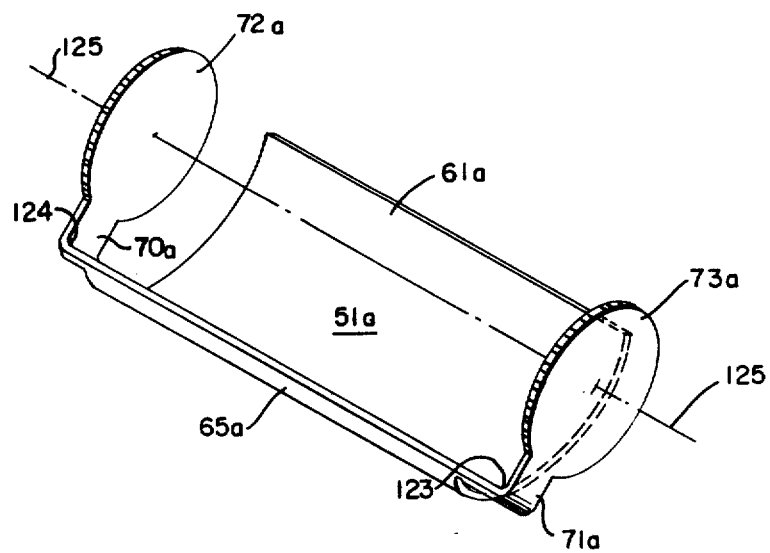
FIG. 11 is an isometric view of the stamped exit shutter element shown in FIG. 10 subsequent to forming for use in the collimator shown in FIG. 1.

Each of the exit shutter elements 51–54 may be made of X-ray absorbent material, such as lead-antimony alloy, for example, or may be made of a thin rigid material coated with X-ray absorbent material, such as sheet steel or molded plastic-laminated with lead, for example. Thus, each of exit shutter elements 51–54 may be stamped and formed or molded and then laminated. Accordingly, as shown in FIG. 10, an exit shutter element, such as 51, for example, may be stamped out as a blank 122 having a generally rectangular portion 51a. The portion 51a has a longitudinal edge portion 65a provided with opposing extensions 70a and 71a, respectively, which are integrally connected to respective spur gear portions 72a and 73a. Subsequently, as shown in FIG. 11, the rectangular portion 51a may be provided with an arcuate curvature, as by means of a mandrel, for example, and the extensions 70a and 71a may be folded along respective lines 123 and 124 to dispose the axial centerline of respective spur gear portions 72a and 73a substantially on the longitudinal centerline 125 of the arcuately curved portion 51a. Alternatively, each of the exit shutter elements, such as 51, for example, may be fabricated integrally with its associated spur gears 72 and 73 in place, as by casting or molding, for example, to provide a very economical means for producing the collimator 34. In either instance, if the fabricated shutter element is not made of X-ray absorbent material, it may be subsequently provided with a lining of X-ray absorbent material, such as lead, for example.

As shown in FIGS. 3–7, the spur gears 72 and 73 of exit shutter element 51 may be provided with respective eccentrically attached pins 102 and 104 which extend outwardly therefrom. The pin 102 protrudes through a slotted end portion of a yoke link arm 106. Arm 106 is integrally formed with a yoke link crossbar 108 which has a central portion fixedly attached to (here integrally formed with) an entrance shutter element 43 of entrance shutter 42. The opposing end portion of crossbar 108 is integrally formed with a relatively short yoke link arm 110. The yoke link crossbar 108 is rotatably supported on a rod 109 having opposing end portions protruding through apertures provided in walls 39 and 41, respectively. Similarly, the pin 104 protrudes through a slotted end portion of a yoke link arm 112. Arm 112 is integrally formed with one end of a yoke link crossbar 114 which has a central portion fixedly attached to entrance shutter element 44 of entrance shutter 42. The opposing end of crossbar 114 is integrally formed with a relatively short yoke link arm 116. The yoke crossbar 114 is rotatably supported on a rod 111 having opposing end portions protruding through side walls 39 and 41, respectively.

Figure 7:
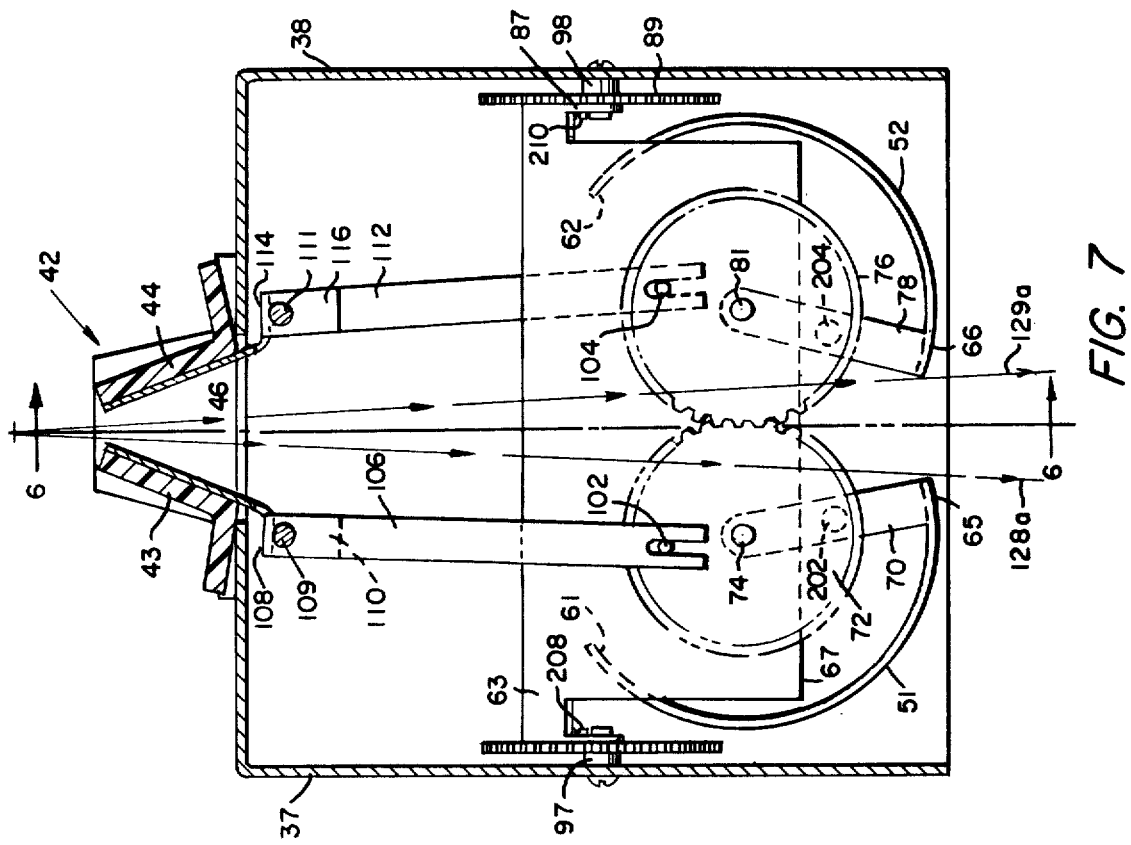
FIG. 7 is a side sectional elevation view similar to FIG. 5 but having the pair of exit shutter elements shown in a substantially closed position.
Figure 6:
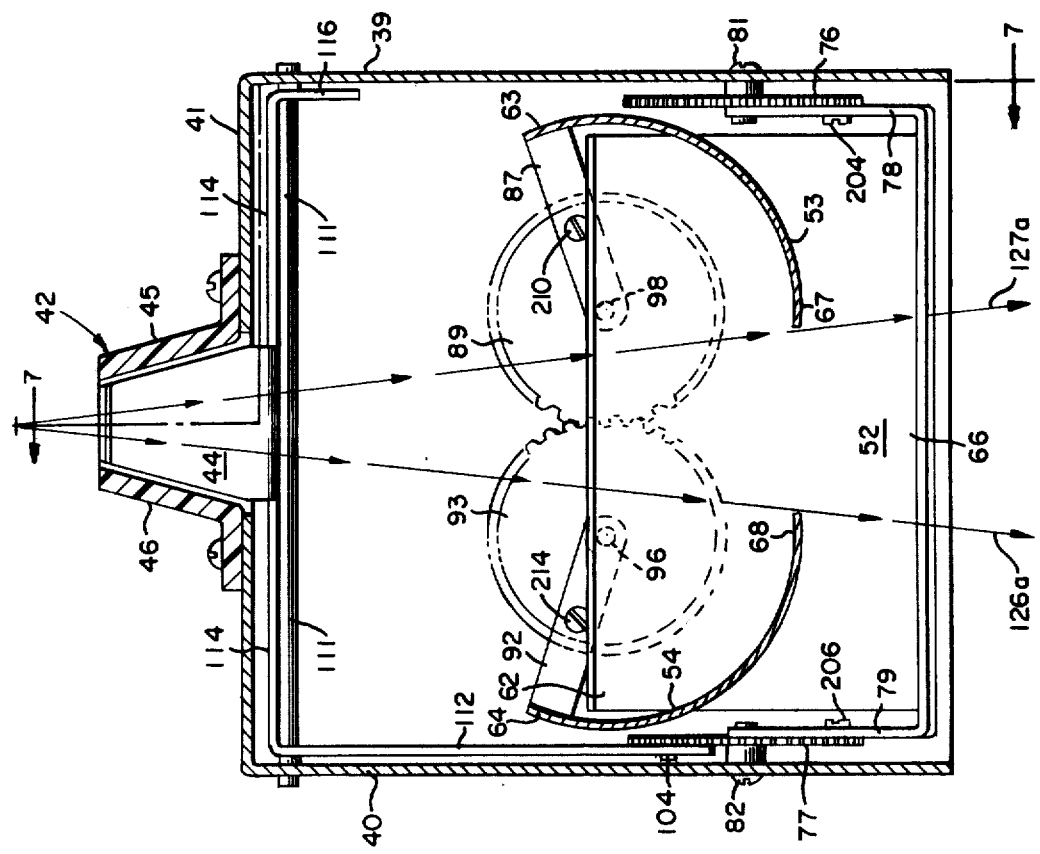
FIG. 6 is a front sectional elevation view similar to FIG. 4 but having the pair of exit shutter elements shown in a partly open position.

Thus, as shown more particularly in FIGS. 4 and 5, the knobs 85 and 100 may be adjusted to rotate the respective pairs of exit shutter elements 51-52 and 53-54 to a substantially fully open position. Consequently, the movable entrance shutter elements 43 and 44 (FIG. 5), respectively, are adjusted in accordance with the adjustment of exit shutter elements 51-52 to permit a widely divergent X-ray beam to enter the housing 36 and to restrict the off focus X-radiation. Accordingly, the widely divergent beam is collimated within housing 36 by the aperture defining edge portion 65, 66, 67 and 68 of the exit shutter elements 51-54 respectivelly, as indicated by arrows 126-129. Also, as shown in FIGS. 6 and 7, the knobs 85 and 100 may be adjusted to rotate the respective pairs of exit shutter elements 51-52 and 53-54 to a more nearly closed position. Note that as the exit shutter elements 51-52 are rotated in counterclockwise and clockwise directions, respectively, the arms 106 and 112 cause the pivotally mounted entrance shutter elements 43 and 44 to define a more closed entrance aperture, as shown in FIG. 7. As a result the pair of movable entrance shutter elements 43 and 44 are adjusted correspondingly to permit passage of a less divergent X-ray beam indicated by arrows 126a-129a, respectively, having outer dimensions defined by the exit shutter elements while maximizing restriction of off-focus X-radiation. Thus, the less divergent X-ray beam entering housing 36 is collimated by the aperture defining edge portions of exit shutter elements 51-54 being suitably positioned for providing the X-ray beam with the desired cross-sectional dimensions.

Figure 8:
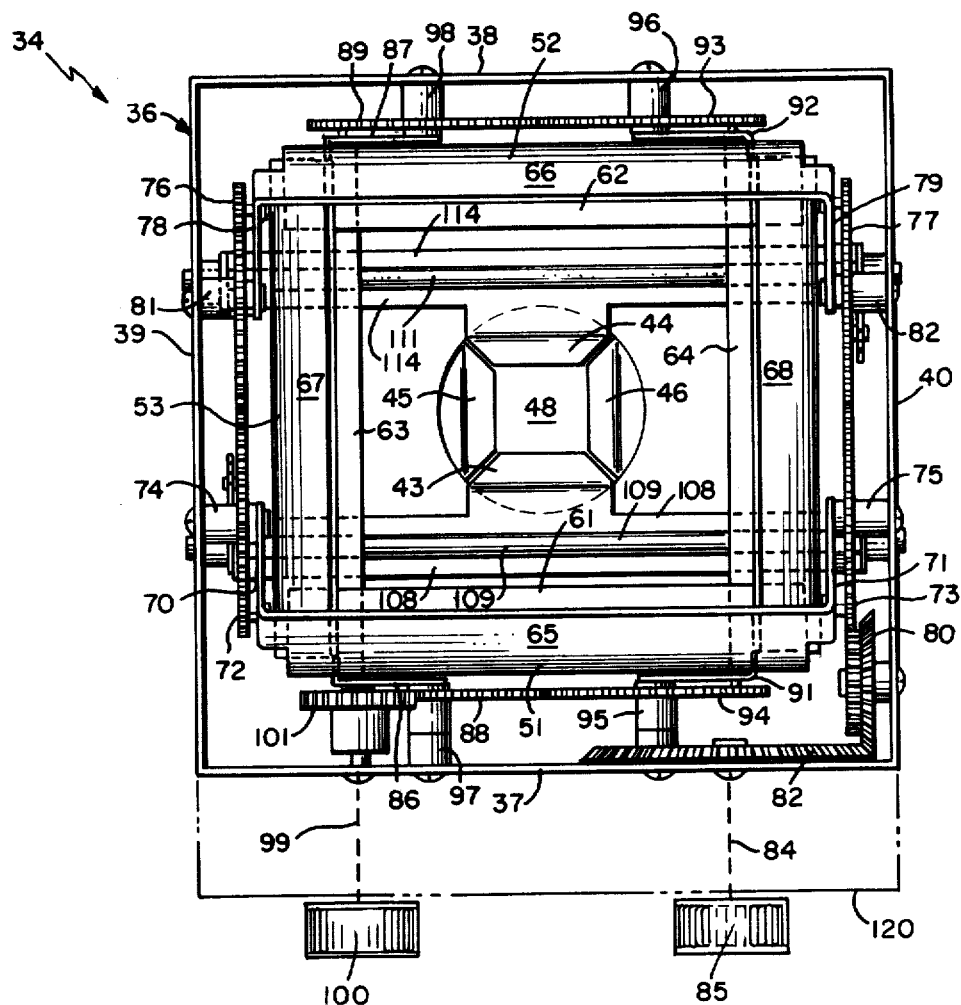
FIG. 8 is a bottom plan view loooking into the exit end of the collimator shown in FIG. 1, with the exit shutter elements in a fully open position.

As shown in FIGS. 2 and 8, there may mounted on front wall 37 a front control panel 120 through which the respective shafts 84 and 99 may extend for rotation by respective knobs 85 and 100 externally of the panel. The control panel 120 also may be provided with respective indicators for signalling when the power is "on," when the X-ray generator 12 is on "hold," and when the respective pairs of exit shutter elements in exit shutter 50 are adjusted. The respective shafts 84 and 99 also may be coupled to respective motors and rotation sensors, such as potentiometers, for example, which are mounted between panel 120 and front wall 37 for automatic operation of the exit shutter 50.

From the foregoing, it will be apparent that all of the objectives of this invention have been achieved by the structures shown and described herein. It also will be apparent, however, that various changes may be made by those skilled in the art without departing from the spirit of the invention as expressed in the appended claims. It is to be understood, therefore, that all matter shown and described herein is to be interpreted as illustrative and not in a limiting sense.

What is claimed is:

1. A radiation collimator, comprising:
   (a) a housing;
   (b) a first and a second pair of shutter elements disposed within the housing and rotatably mounted with respect to the housing, each one of such shutter elements having a surface with an edge portion thereof defining a different peripheral portion of an aperture, the surfaces of the first pair of shutter elements being adapted to rotate within a space disposed between the surfaces of the second pair of shutter elements and the surfaces of the second pair of shutter elements being adapted to rotate within a space disposed between the surfaces of the first pair of shutter elements.

2. The collimator recited in claim 1 wherein each one of the shutter elements has an arcuately shaped surface, such arcuately shaped surface being concave with respect to a region bounded by the first and second pairs of shutter elements.

3. The collimator recited in claim 2 wherein each one of the shutter elements has a wall disposed along a portion of a generally cylindrical surface.

4. The collimator recited in claim 3 wherein each one of the shutter elements is rotatable about the longitudinal axis of the generally cylindrical surface associated therewith.

5. The collimator recited in claim 4 wherein each one of the shutter elements includes a gear attached thereto in stationary relationship therewith, such gear having a plane orthogonal to the longitudinal axis of the generally cylindrical surface associated with such one of the shutter elements, and wherein each one of such gears has a central shaft rotatable supporting such gear to the housing.

6. The collimator recited in claim 5 including means for positioning the gears of the first pair of shutter elements in engaging relationship and the gears of the second pair of shutter elements in engaging relationship.

7. The collimator recited in claim 1 including a pair of entrance shutter elements pivotally mounted with respect to the housing and coupled directly to the first pair of shutter elements.

8. The collimator recited in claim 7 including a pair of coupling arms connected to the pair of entrance shutter elements at first portions of the arms and connected to the first pair of shutter elements at second portions of the arms, such pair of coupling arms being pivotally mounted to the housing at a point between the first and second portions thereof.

9. The collimator recited in claim 8 wherein each one of the shutter elements has a generally semi-cylindrical surface and a gear affixed in stationary relationship therewith, such gear having a surface disposed orthogonal to the longitudinal axis of the semi-cylindrical surface and having an axis of rotation coaxial with such longitudinal axis, such axis of rotation being rotatably connected to the housing and wherein the second portions of the pair of coupling arms are connected to the surfaces of the gears of the first pair of shutter elements.

10. A radiation collimator comprising;
    (a) a housing;
    (b) a pair of opposing exit shutter elements, each one thereof having a radiation absorbing surface and a gear disposed in stationary relationship thereto, such gear having a surface disposed in a plane orthogonal to the radiation absorbing surface and having engageable teeth disposed along an edge of such gear orthogonal to the surface of the gear, such gear having a shaft normal to the surface of the gear and rotatably mounted to the housing, such pair of opposing exit shutter elements being mounted within the housing with the teeth of one of the gears of one of the exit shutter elements engaged with the teeth of the gear of the other one of the exit shutter elements; and (c) a pair of entrance shutter elements pivotally mounted to the housing; a pair of linkage arms, such arms being connected to the pair of entrance shutter elements at a first portion thereof and being connected to the surface of said gears at a second portion thereof and wherein such arms are pivotally connected to the housing at a point between such first and second portions.

11. A beam limiting device comprising:

two orthogonal pairs of opposing shutter elements disposed for defining a beam collimating aperture having an axial centerline, each of said elements having cylindrically curved wall portions disposed orthogonally to said axial centerline and longitudinal edge portions disposed for defining respective peripheral portions of said aperture; and means disposed adjacent at least one arcuate end of each of said cylindrically curved wall portions for rotating each of said shutter elements about its longitudinal axis and moving said longitudinal edge portions relative to one another for adjusting the size of the aperture.

12. A beam limiting device comprising:

two orthogonal pairs of opposing cylindrically curved shutter elements disposed for defining a rectangular aperture, the elements of each of said pairs having respective longitudinal edge portions disposed in opposing relationship with one another between said cylindrically curved elements of the other pair and supported in spaced encircling relationship with respective arcuate ends thereof; and means disposed adjacent at least one arcuate end of each of the elements of said pairs for rotating said each of the elements in respective opposing directions about its longitudinal centerline and adjusting the size of said aperture.

13. A beam limiting device as set forth in claim 12 wherein said means includes a respective gear disposed adjacent said arcuate ends of each of the elements and having axes of rotation substantially aligned with said longitudinal axes of the elements.

14. A beam limiting device as set forth in claim 13 wherein said gears are fixedlly attached to said cylindrically curved elements for rotation as respective unitary structures.

15. A beam limiting device comprising:

a radiation shielded housing including an entrance wall having disposed therein entrance aperture means for permitting passage of a radiation beam into the housing;

exit shutter means disposed in the housing for providing collimation of said beam and including two orthogonal pairs of opposing cylindrically curved shutter elements, the elements of each pair having respective longitudinal edge portions disposed in opposing relationship between the cylindrically curved elements of the other pair and supported in spaced enveloping relationship with respective arcuate ends thereof; and means disposed adjacent at least one arcuate end of each of the shutter elements of said respective pairs for rotating said each of the elements in respective opposing directions and adjusting the size of said aperture.

16. A beam limiting device as set forth in claim 15 wherein said entrance aperture means comprises an entrance shutter having two orthogonal pairs of opposing entrance shutter elements disposed for defining a rectangular entrance aperture, the respective entrance shutter elements of one of said pairs being supported for movement relative to one another and directly connected to corresponding shutter elements of the exit shutter means for corresponding adjustment therewith.

17. A radiation collimator comprising:

(a) a housing;

(b) a first and a second pair of shutter elements disposed within the housing, the first pair of shutter elements being rotatably mounted with respect to the housing about a first pair of parallel axes and the second pair of shutter elements being rotatably mounted with respect to the housing about a second pair of parallel axes, the first pair of parallel axis being perpendicular to the second pair of parallel axes, each one of such shutter elements having a concave surface with a pair of edge portions thereof parallel to the axis of rotation of such shutter element, one of such edge portions thereof defining a different peripheral portion of an aperture, one of the pair of edge portions of the surfaces of the first pair of shutter elements being adapted to rotate within a space disposed between the surfaces of the second pair of shutter elements and one of the pair of edge portions of the surfaces of the second pair of shutter elements being adapted to rotate within a space disposed between the surfaces of the first pair of shutter elements.

* * * * *